(12) United States Patent
 Tuttle

(10) Patent No.: US 11,020,538 B2
(45) Date of Patent: Jun. 1, 2021

(54) ANESTHESIA NEEDLE ASSEMBLY AND METHODS

(71) Applicant: TuttleNumbNow LLC, Provo, UT (US)

(72) Inventor: Gregory K. Tuttle, Provo, UT (US)

(73) Assignee: TuttleNumbNow LLC, Provo, UT (US)

( * ) Notice: Subject to any disclaimer, the term of this patent is extended or adjusted under 35 U.S.C. 154(b) by 0 days.

(21) Appl. No.: 15/829,538

(22) Filed: Dec. 1, 2017

(65) Prior Publication Data

US 2018/0126093 A1 May 10, 2018

Related U.S. Application Data

(63) Continuation of application No. PCT/US2016/053901, filed on Sep. 27, 2016.

(60) Provisional application No. 62/233,640, filed on Sep. 28, 2015, provisional application No. 62/289,567, filed on Feb. 1, 2016.

(51) Int. Cl.
*A61M 5/32* (2006.01)
*A61M 5/158* (2006.01)
*B21G 1/08* (2006.01)

(52) U.S. Cl.
CPC ............ *A61M 5/3287* (2013.01); *A61M 5/32* (2013.01); *A61M 5/3202* (2013.01); *A61M 5/3286* (2013.01); *A61M 5/158* (2013.01); *A61M 2005/3284* (2013.01); *A61M 2207/00* (2013.01); *A61M 2207/10* (2013.01); *A61M 2210/02* (2013.01); *A61M 2210/0625* (2013.01); *B21G 1/08* (2013.01)

(58) Field of Classification Search
CPC ........ A61M 5/3278; A61M 2005/3284; A61M 5/3287; A61M 2207/00; A61M 2207/10; A61M 2210/02; A61M 2210/0625; A61M 5/158; A61M 5/32; A61M 5/3202; A61M 5/3286

See application file for complete search history.

(56) References Cited

U.S. PATENT DOCUMENTS

| 780,756 A | * | 1/1905 | Lakin | |
|---|---|---|---|---|
| 907,210 A | * | 12/1908 | Williams | |
| 3,884,230 A | | 5/1975 | Wulff | |
| 4,188,950 A | * | 2/1980 | Wardlaw | A61M 5/2033 604/111 |
| 4,266,544 A | * | 5/1981 | Wardlaw | A61M 5/3278 604/110 |

(Continued)

OTHER PUBLICATIONS

International Search Report issued in PCT Application No. PCT/US2016/053901 dated Dec. 2, 2016.

*Primary Examiner* — Theodore J Stigell
(74) *Attorney, Agent, or Firm* — Arent Fox LLP

(57) ABSTRACT

Systems and methods are disclosed for bending a needle. A device for bending a needle is disposed around a needle and coupled to an injection device. A force is exerted on the needle to cause the needle to bend upon a bending trough of the device. The device includes a proximal end to interface with the injection device and a distal end having the bending trough. The bending trough is configured to improve bending and prevent breaking of the needle by providing a rounded surface upon which the needle is bent.

13 Claims, 8 Drawing Sheets

(56) References Cited

U.S. PATENT DOCUMENTS

| | | | | |
|---|---|---|---|---|
| 4,269,056 | A * | 5/1981 | Kozinski | B21D 7/063 |
| | | | | 72/459 |
| 4,634,428 | A * | 1/1987 | Cuu | A61M 5/3213 |
| | | | | 206/365 |
| 4,728,320 | A * | 3/1988 | Chen | A61M 5/3213 |
| | | | | 604/110 |
| 5,405,330 | A | 4/1995 | Zunitch et al. | |
| 5,437,640 | A * | 8/1995 | Schwab | A61M 5/32 |
| | | | | 604/116 |
| 6,494,713 | B1 | 12/2002 | Pond | |
| 9,457,155 | B2 * | 10/2016 | Mathiasson | A61M 5/3216 |
| 2003/0045839 | A1 | 3/2003 | Yoshio et al. | |
| 2007/0016146 | A1 | 1/2007 | Yang | |
| 2007/0149924 | A1 * | 6/2007 | Marsh | A61M 5/002 |
| | | | | 604/117 |
| 2007/0185460 | A1 | 8/2007 | Vedrine et al. | |
| 2008/0058717 | A1 * | 3/2008 | Spector | A61C 5/62 |
| | | | | 604/117 |
| 2010/0198152 | A1 * | 8/2010 | Haindl | A61M 5/3216 |
| | | | | 604/110 |
| 2011/0295218 | A1 * | 12/2011 | Kjeldsen | A61M 5/158 |
| | | | | 604/272 |
| 2011/0319831 | A1 * | 12/2011 | Bode | A61M 5/3202 |
| | | | | 604/192 |
| 2013/0150680 | A1 * | 6/2013 | Larson | A61B 1/00119 |
| | | | | 600/205 |

\* cited by examiner

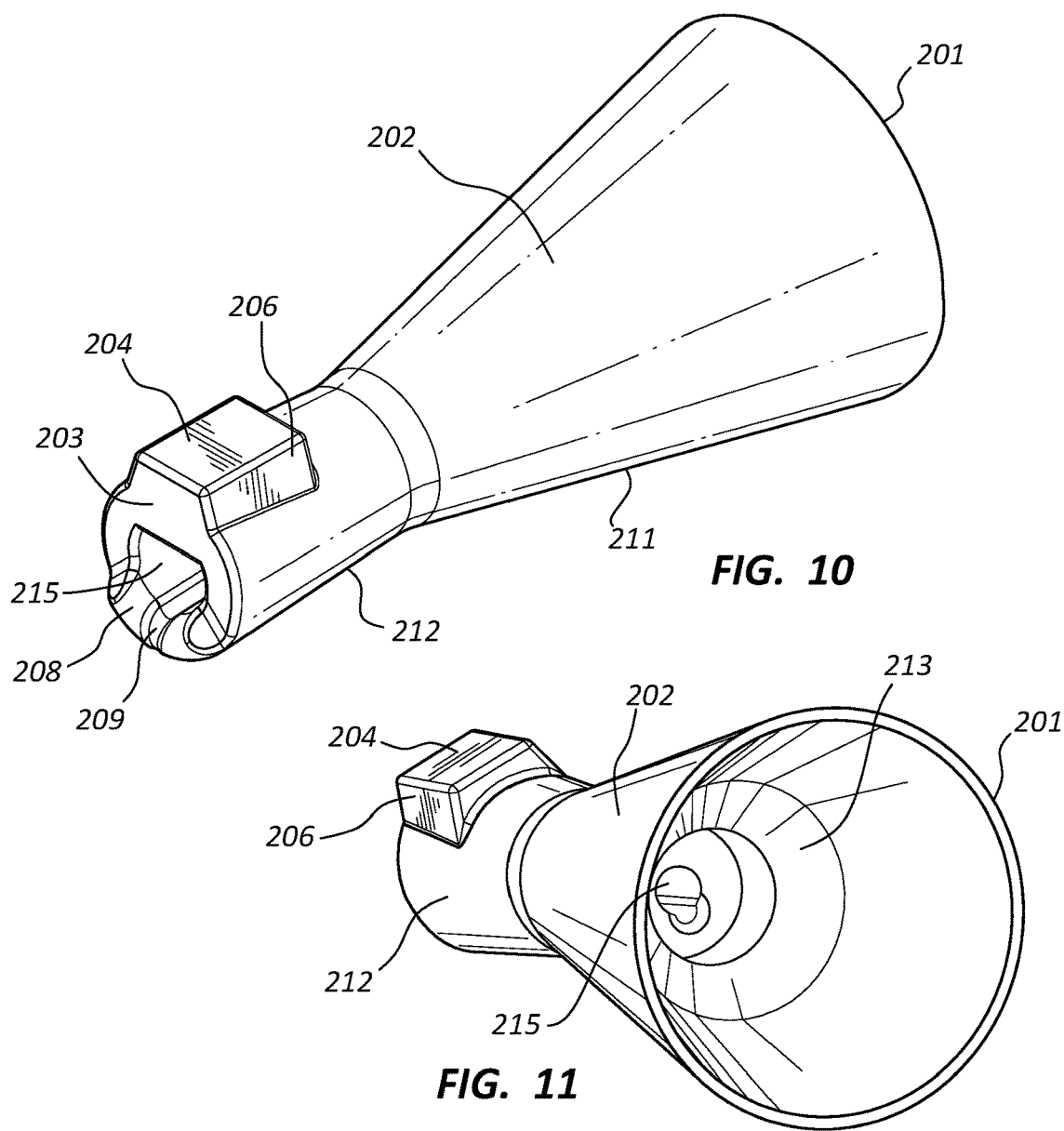
FIG. 10
FIG. 11
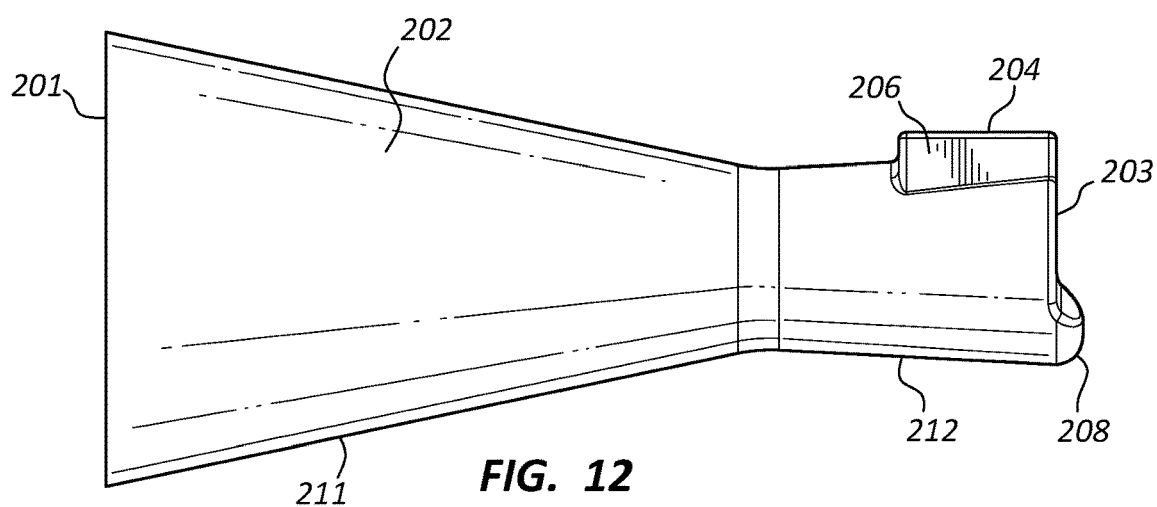
FIG. 12

ANESTHESIA NEEDLE ASSEMBLY AND METHODS

RELATED APPLICATIONS

This application is a continuation of currently pending PCT Application No. PCT/US2016/053901 filed on Sep. 27, 2016 and titled, "Systems and Methods for Bending a Needle," which, in turn, claims priority to U.S. Provisional Application No. 62/233,640, filed on Sep. 28, 2015 and titled "One-Step Localized Interosseous Anesthesia Method and Apparatus," and U.S. Provisional Application No. 62/289,567, filed on Feb. 1, 2016 and titled "Systems and Methods for Bending a Needle," all of which are hereby incorporated by reference in their entireties.

TECHNICAL FIELD

This disclosure relates to methods and systems for bending a medical device. More particularly, this disclosure relates to methods and systems for bending needles of fluid dispensing devices such as syringes. In some procedures, such as dental procedures, for example, a desired injection site may be difficult to access. A bent needle may facilitate access to various difficult injection sites.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 10 is a perspective view of another embodiment of a needle guide for bending a medical device;

FIG. 11 is another perspective view of the needle guide of FIG. 10;

FIG. 12 is a side view of the needle guide of FIG. 10;

DETAILED DESCRIPTION OF EMBODIMENTS

Figure 1:
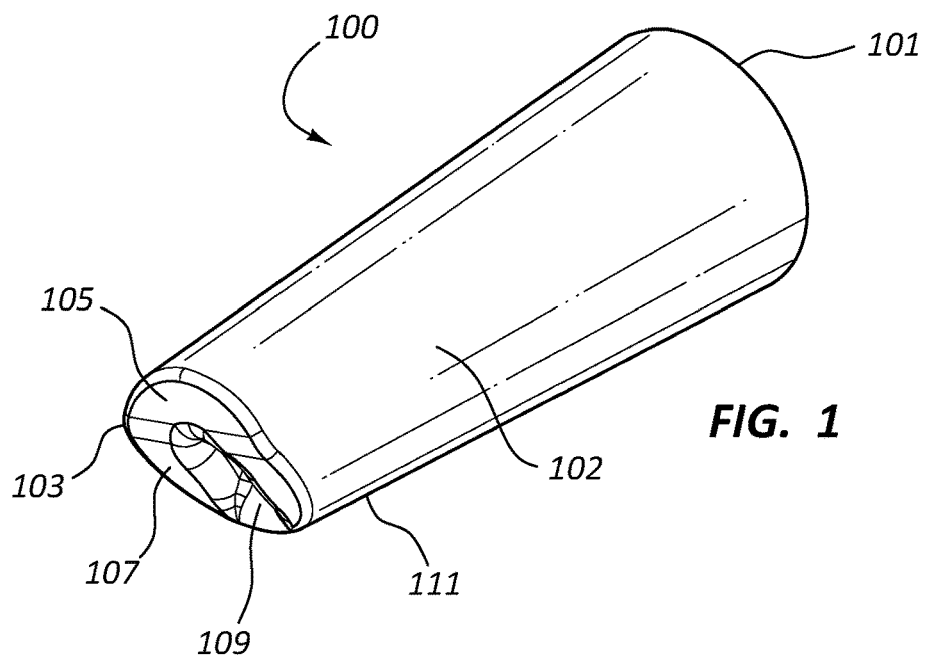
FIG. 1 is a perspective view of a needle guide for bending a medical device.

Embodiments and arrangements disclosed herein may include one or more devices for bending a medical device. In certain embodiments, a bending device—such as a needle guide—is disposed around a needle of a fluid dispensing device (or "injection device") and coupled to a needle hub of the fluid dispensing device. Once the bending device is coupled to the needle hub or other component of the fluid dispensing device, the needle may be bent upon a surface or portion of the bending device. The bending device may thus facilitate bending of the needle at point offset a distance from the needle hub. This distance may prevent or minimize the likelihood of breaking a rigid coupling between the needle and the needle hub which could, in turn, render the fluid dispensing device inoperable. In some embodiments, the bent needle comprises a curved bent section to prevent kinking and concentrated stress on the needle. A medical professional may then use the fluid dispensing device comprising the bent needle to access otherwise difficult to reach injection sites in the body. For example, a dentist, oral surgeon, or the like may utilize a bent needle to target delivery of anesthetic to a specific location for more efficient delivery.

Although various disclosures herein may reference a fluid dispensing device such as a syringe, the bending devices and methods disclosed herein may be used in conjunction with any number of medical devices. Furthermore, as used herein, a needle may refer to any elongate medical device that may be used for inserting into a patient. Exemplary needles within the scope of this disclosure include, but are not limited to, a hollow metal tube, a hollow plastic tube, a solid metal elongate tool, or a solid plastic elongate tool.

For simplicity and clarity of illustration, the figures illustrate the general manner of construction, and descriptions and details of well-known features and techniques may be omitted to avoid unnecessarily obscuring the discussion of the described embodiments. Additionally, elements in the drawing figures are not necessarily drawn to scale. For example, the dimensions of some of the elements in the figures may be exaggerated relative to other elements to help improve understanding of the disclosed embodiments. The same reference numerals in different figures denote the same elements, while similar reference numerals may, but do not necessarily, denote similar elements.

The terms "first," "second," and the like in the description and in the claims, if any, are used for distinguishing between similar elements and not necessarily for describing a particular sequential or chronological order. It is to be understood that the terms so used are interchangeable under appropriate circumstances such that the embodiments of the invention described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method. Furthermore, the terms "comprise," "include," "have," and any variations thereof are intended to cover a non-exclusive inclusion, such that a process, method, article, or apparatus that comprises a list of elements is not necessarily limited to those elements, but may include other elements not expressly listed or inherent to such process, method, article, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein. Objects described herein as being "adjacent" each other may be in physical contact with each other, in close proximity to each other, or in the same general region or area as each other, as appropriate for the context in which the phrase is used.

The phrases "connected to" and "coupled to" are broad enough to refer to any suitable coupling or other form of interaction between two or more entities, including mechanical, fluidic, and thermal interaction. Two components may be coupled to each other even though they are not in direct contact with each other. The phrases "attached to" or "directly attached to" refer to interaction between two or more entities which are in direct contact with each other and/or are separated from each other only by a fastener of any suitable variety (e.g., an adhesive).

The terms proximal and distal refer to opposite ends of a device or component. With reference to medical devices, the proximal end refers to the end nearest to a practitioner during use, while the distal end refers to the opposite end along a longitudinal axis. For example, the distal end of a needle refers to the sharpened end configured for insertion into a patient.

The systems and methods disclosed herein may be used for interosseous injection, or injections between bone structures or for intraosseous injections, or injections within bone. Any method, device, system, or kit disclosed herein may be used interosseously or intraosseously. Further, U.S. Provisional Application No. 62/233,640, incorporated by reference above, references interosseous procedures. The disclosure of that application may be analogously applied to intraosseous procedures as well. Thus, disclosure in the underlying provisional application to interosseous methods, devices, systems, or kits may be applied to intraosseous application as well.

FIG. 1 illustrates a bending device, needle guide 100, which comprises a proximal end 101, a distal end 103, a distal-most surface 105 of the distal end 103, a truncated surface 107 of the distal end 103, a bending trough 109, and an exterior surface 111 of the body member 102 of the needle guide 100. As further detailed below, the needle guide 100 may be utilized to facilitate bending of a medical device, such as a needle. The needle guide 100 defines a longitudinal axis extending between the proximal end 101 and the distal end 103. In some embodiments, the needle guide 100 may comprise any rigid material including, but not limited to, plastic or metal. In some embodiments, the needle guide 100 comprises a material that is sanitizable with standard medical cleaning supplies. Further, the needle guide 100 may comprise one or more grip surfaces to improve a user's ability to control the needle guide 100 during procedures such as pushing or pulling on the needle guide 100. In some of these embodiments, the one or more grip surfaces may be disposed on the exterior surface 111 of the needle guide 100. The grip surfaces may be positioned adjacent the distal end 103 of the needle guide 100.

In some embodiments, the bending trough 109 comprises a bending surface that is convexly curved with respect to at least one plane. Thus, the profile of the bending trough 109, viewed with respect to a plane normal to the surface of the bending trough, may comprise an arc, such as defined by a portion of a circle, an ellipse, or a parabola. The bending trough 109 may provide a profile or shape for bending a medical device such as a needle. A needle or other medical device may be plastically deformed by forcing the needle into contact with the bending trough 109. A needle bent through contact with the bending trough 109 may thus partially conform to the shape of the bending trough 109. The convexly curved surface may thus provide a form or guide for bending the needle, imparting a curve profile to the needle to distribute a bending stress along a length of the needle and control the position of the bend along a length of the needle. This may prevent or reduce kinking of a lumen of the needle and/or breaking of the needle at a bending region. In one aspect, the bending trough 109 may be formed as an extending concave surface, which may be configured to receive a portion of the needle or other medical device. In some embodiments, the bending trough 109 comprises a longitudinal groove to restrict lateral movement of the needle during bending.

Figure 6:
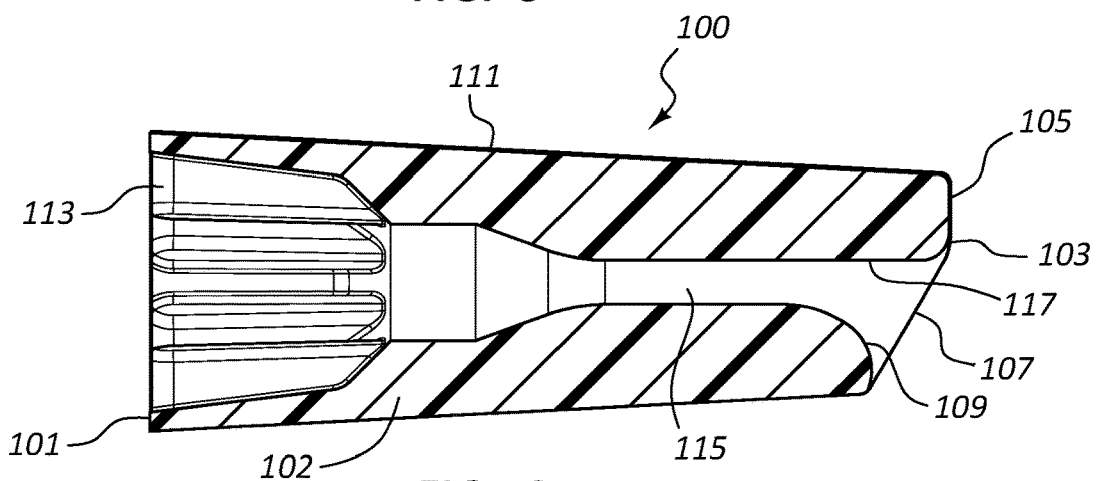
FIG. 6 is a cross-sectional view from the side of the needle guide of FIG. 1.
Figure 8:
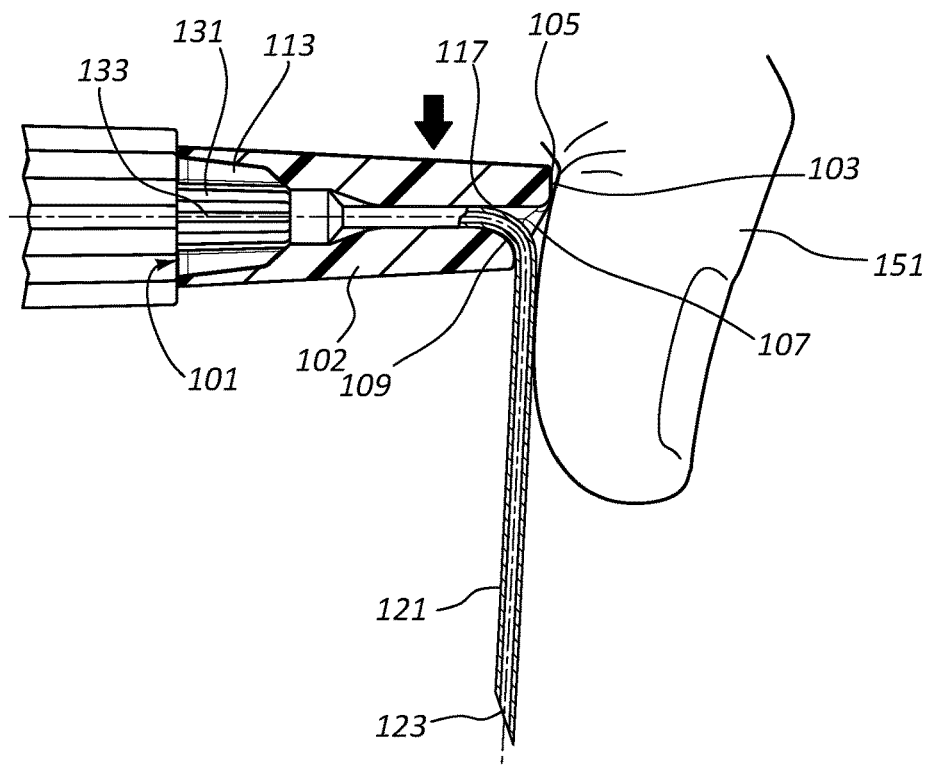
FIG. 8 is another cross-sectional view from the side of the needle guide and the medical device of FIG. 7.

In some embodiments, such as the embodiment of FIG. 1, the bending trough 109 may be positioned proximal of the distal-most surface 105 of the distal end 103 of the needle guide 100, along the longitudinal axis, leaving a portion of the body member 102 of the needle guide 100, interface surface 117 (not shown in FIG. 1), disposed above the bending trough 109 when the needle guide 100 is oriented with the bending trough 109 downward. This is also shown in FIG. 6, which is a cross-sectional side view of the needle guide 100 of FIG. 1. The interface surface 117 is also shown in FIG. 8 which is a cross-sectional side view of the needle guide 100 of FIG. 1 with a needle 121 disposed within the lumen 115 of the needle guide 100. As shown in FIGS. 1, 6, and 8, the needle guide 100 interface surface 117 may provide a bearing surface for transferring force applied by a user to the needle guide 100 to a needle (such as needle 121) disposed within the lumen 115 of the needle guide 100. For example, a downward force applied to the needle guide 100, relative to the orientation shown by the arrow in FIG. 6, would displace the interface surface 117 toward the needle 121, transferring the downward force to the needle 121 at the bend in the needle 121. The direction of an exemplary downward force is shown by the arrow of FIG. 8. In some embodiments, the interface surface 117 of the needle guide 100 may have a groove or other element for holding a bent needle in place during the transfer of force described.

Referring again to FIG. 1, the needle guide 100 may be configured to be placed over a distal end of the needle and slid proximally to an interface with a component of an injection device. The needle guide 100 may be independent from the injection device, or it may be an integral component of an injection device.

In embodiments wherein the needle guide 100 is an integral component of an injection device, including a needle, the needle guide 100 may not be rigidly coupled directly to the needle adjacent the bending trough 109. For example, the needle may be fixed to a needle hub, for example by glue, but not fixed to the needle guide 100 within the lumen (115 of FIG. 6). In some embodiments, the needle guide 100 may form a loose fit around the needle without coupling directly to the needle. An offset between rigid coupling of the needle and the location of the bending trough 109, may introduce additional tolerance for bending into the assembly, by allowing the needle to flex or displace along a distance away from the bending trough 109. This offset may be present both in embodiments wherein the needle guide 100 is a separate component from the needle and needle hub assembly and embodiments wherein the needle guide 100 is an integral component of a needle hub.

Figure 2:
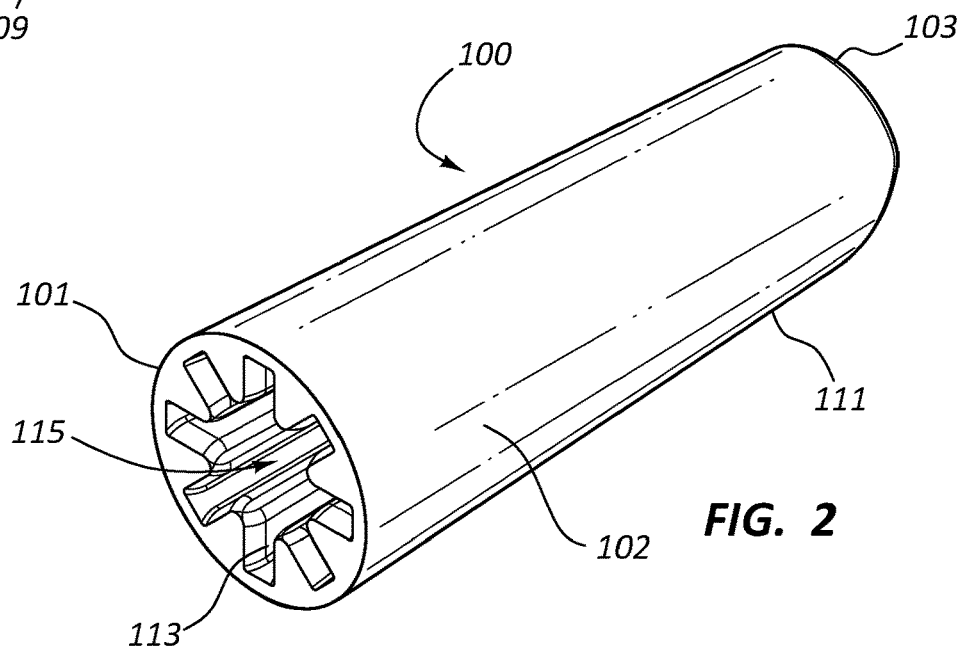
FIG. 2 is another perspective view of the needle guide of FIG. 1.

FIG. 2 illustrates the needle guide 100 of FIG. 1 from a perspective view of the proximal end 101 of the needle guide 100. In the view of FIG. 2, the lumen 115 is shown extending into the body of the needle guide 100 from the proximal end 101. An injection device interface 113, comprising ridges for coupling with an injection device is also shown. The distal end 103 and the exterior surface 111 of the needle guide 100 are also indicated.

The injection device interface 113 may be configured to couple the needle guide 100 to an injection device. In some embodiments, the injection device interface 113 is configured to form a friction fit with a needle hub of an injection device. In other embodiments, the injection device interface 113 may form a snap fit connection with a needle hub of the injection device. The injection device interface 113 may be configured in any shape to mate with an element of the injection device. In some embodiments, the injection device interface 113 prohibits rotation of the needle guide 100 around the longitudinal axis (with respect to the injection device) when coupled to an injection device.

The lumen 115 may extend the length of the needle guide 100 and may be defined by an interior surface of the body member 102 of the needle guide 100. In some embodiments, a diameter of the lumen 115 may be slightly larger than a diameter of a needle to be bent, thus forming a loose fit around the needle. In the illustrated embodiment, the lumen 115 is in communication with the bending trough 109 as shown in FIG. 1.

Figure 3:
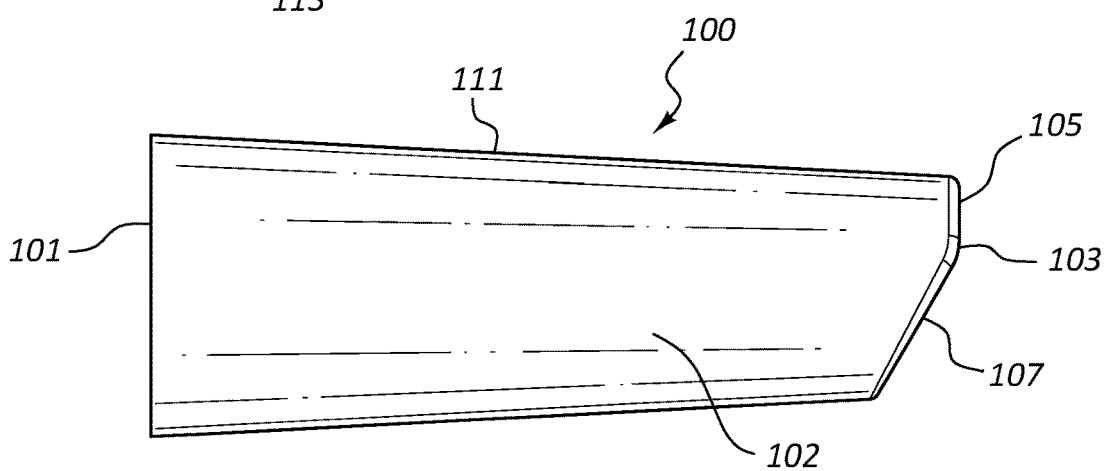
FIG. 3 is a side view of the needle guide of FIG. 1.
Figure 7:
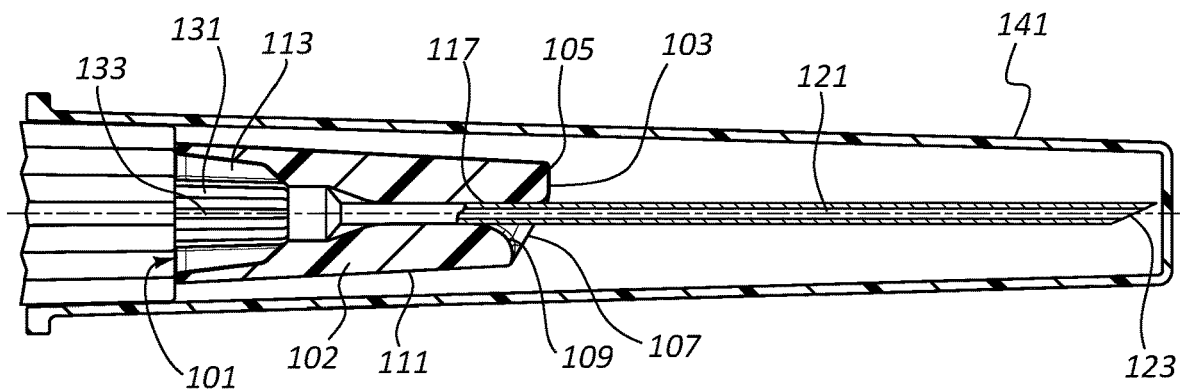
FIG. 7 is a cross-sectional view from the side of the needle guide of FIG. 1 assembled with a medical device.

FIG. 3 is a side view of the needle guide 100 of FIG. 1 illustrating the proximal end 101, the distal end 103, the distal-most surface 105, the truncated surface 107, and the exterior surface 111 of the needle guide 100. The length of the needle guide 100 may be greater than 2 millimeters. The length of the needle guide 100 may be greater than 3 millimeters. The length of the needle guide 100 may be greater than 3.5 millimeters. In other embodiments, the length of the needle guide 100 is about 4 millimeters. In some embodiments, the length of the needle guide 100 is between 3 millimeters and 5 millimeters. In some of these embodiments, the length of the needle guide needle guide 100 is between 3.5 and 4.5 millimeters. In some embodiments, the length of the needle guide 100 may be measured from the proximal end 101 to the distal end 103. In other embodiments, the length of the needle guide may be defined as the distance from the bending trough 109 to a coupling region 133 of a needle hub 131 as shown in FIG. 7. The distance between the bending trough 109 and the coupling region 133 may also correspond to the magnitude of the offset between a needle hub (wherein a needle may be fixed to the needle hub) and the location on the needle wherein the needle is bent along the bending trough 109 of the needle guide 100.

Figure 4:
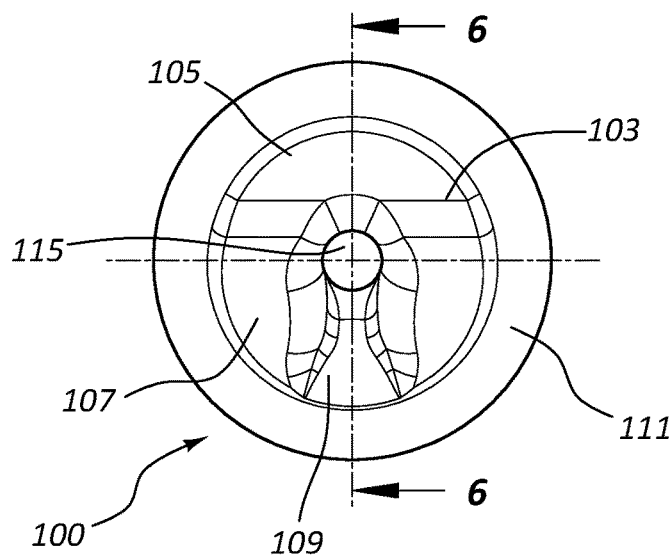
FIG. 4 is an end view of the needle guide of FIG. 1 from a distal end.

FIG. 4 is an end view of the distal end 103 of the needle guide 100 of FIG. 1 showing the distal-most surface 105, the truncated surface 107, the bending trough 109, the exterior surface 111, and the lumen 115. As shown, the exterior surface 111 may be visible from this end view because, in the shown embodiment, the distal end 103 is narrower than the proximal end 101 of FIG. 1. In other words, the needle guide 100 may have a conical or frusto-conical shape. In other embodiments, the needle guide 100 may have any cross-sectional shape (viewed from the longitudinal axis or an axis normal to the longitudinal axis) including, but not limited to, a triangle, a square, a rectangle, an hourglass shape, a trapezoid, a parallelogram, a circle, an ellipse, a polygon, or the like. For example, in some instances when viewed from the end, the needle guide 100 may comprise one or more bulbous portions (such as the rounded portions of an hourglass shape) to provide a shape and surface for gripping the needle guide 100. As illustrated, the bending trough 109 may have a topography to direct the position of the needle to a proper bending location when bending a needle upon the bending trough 109. Also shown is a rounded surface where the lumen 115 intersects with the distal end 103. In other embodiments, the needle guide 100 may not have rounded surfaces where the lumen 115 intersects the distal end 103.

Figure 5:
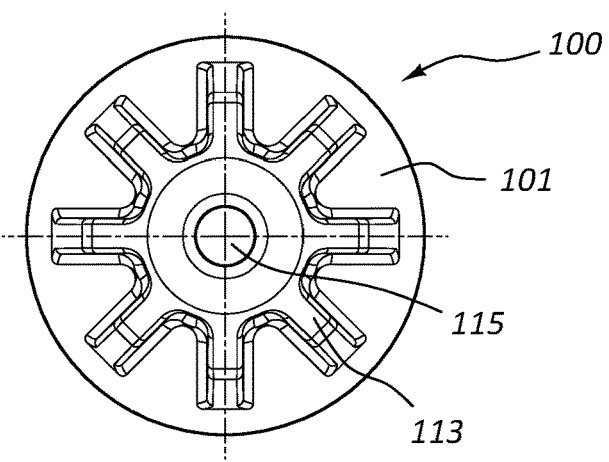
FIG. 5 is an end view of the needle guide of FIG. 1 from a proximal end.

FIG. 5 is an end view of the proximal end 101 of the needle guide 100 of FIG. 1 showing the injection device interface 113 and the lumen 115. As shown, the injection device interface 113 may extend a length distally from the proximal end 101 and terminate proximal of the distal end 103 of the needle guide 100.

FIG. 6 is a cross-sectional view of the needle guide 100 along line 6 of FIG. 4 showing the proximal end 101, the distal end 103, the body member 102, the distal-most surface 105, the truncated surface 107, the bending trough 109, the exterior surface 111, the injection device interface 113, the lumen 115, and the interface surface 117. As discussed above, the bending trough may be an extended concave surface, which may be configured to receive a portion of the needle or other medical device. The the interface surface 117 may be disposed above the bending trough 109 when the needle guide 100 is oriented with the bending trough 109 downward. The interface surface 117 may provide a bearing surface for transferring force applied by a user to the needle guide 100 to a needle 121 disposed within the lumen 115 of the needle guide 100. In some embodiments, the interface surface 117 may thus be disposed directly across, or at 180° to, the bending trough 109. Also shown, a diameter of the lumen 115 may vary along the length of the needle guide 100. In some embodiments the diameter of the lumen 115 is narrowest adjacent the bending trough 109. As shown in FIG. 6, the concave surface of bending trough 109 may include a proximal portion 109A and a distal portion or end 109B that may be angled substantially perpendicular to the proximal portion 109A.

FIG. 7 is a cross-sectional view of the needle guide 100 of FIG. 1 assembled with an injection device comprising a needle hub 131, a needle coupling region 133 wherein a needle 121 is coupled to the needle hub 131, a distal end 123 of the needle 121, and a cap 141. As shown, the injection device interface 113 may interact with the needle hub 131 to couple the needle guide 100 to the injection device. In some embodiments, the injection device interface 113 may loosely couple to the injection device. In other embodiments, the injection device interface 113 may couple to the injection device using one or more of a friction fit, a snap fit, a permanent weld, and an adhesive. As illustrated, the needle guide 100 may encapsulate the needle hub 131 and the proximal end 101 may contact another element of the injection device. In other embodiments, a portion of the needle hub 131 may be visible proximal to the proximal end 101 of the needle guide 100. The needle 121 may be coupled to the coupling region 133 of the needle hub 131 using a rigid coupling system including, but not limited to, adhesive, melting, and/or welding.

In some embodiments, the needle guide 100 of FIG. 1 may be integrally formed with the needle hub 131. For example, the needle guide 100 and the needle hub 131 may be formed of a single piece of material such as plastic or metal. In some of these embodiments, the needle 121 may be rigidly coupled to a proximal segment of the single piece of material and a distal segment may comprise the features described herein for the bending device 100, wherein the distal segment provides a distance to offset the proximal segment from the bending trough 109.

FIG. 8 illustrates the assembly of FIG. 7 with the cap 141 removed and the needle 121 is bent by a user's finger 151. FIG. 8 further shows a bending region 125 of the needle 121 bent upon the trough 109 of the needle guide 100. As in the illustrated embodiments, the trough 109 may cause the bending region 125 to follow the curve of the trough 109 to an angle approximately normal to the longitudinal axis of the needle guide 100. In other embodiments, a user may bend the needle 121 to any desired angle from 0 degrees to 180 degrees including about 30 degrees, about 45 degrees, about 60 degrees, about 120 degrees, about 135 degrees, and about 150 degrees. As shown in the illustration, a user's finger 151 may be used to apply a force on the needle 121 from a direction opposite the trough 109 to cause the needle 121 to bend upon the trough 109. The illustration also shows that the user's finger 151 may bend the needle 121 without being placed in proximity to the distal end 123 of the needle 121. In other embodiments, a user may bend the needle 121 by advancing the cap 141 distally and exerting a downward force on the cap 141 such that an interior surface of the cap 141 transfers the downward force onto the needle 121, thus bending the needle 121 without direct contact between the user and the needle 121. Similarly, positioning the cap 141 over the distal end of the needle 121 and rotating the cap 141 with respect to the needle 121 such that the needle 121 bends on the bending trough 109 is likewise within the scope of this disclosure. In other embodiments, a user may press the needle 121 against another surface to provide a normal force to bend the needle 121 upon the bending trough 109.

Figure 9:
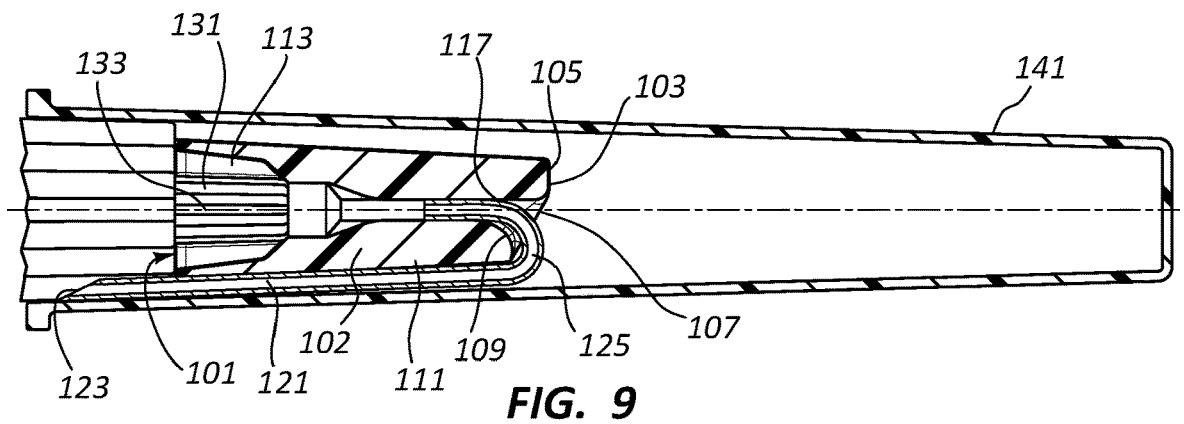
FIG. 9 is another cross-sectional view from the side of the needle guide and the bent medical device of FIG. 7.

FIG. 9 illustrates the assembly of FIG. 7 wherein the needle 121 is bent about 180 degrees. In some embodiments, the needle guide 100 comprises a rounded surface connecting the bending trough 109 to the exterior surface 111 such that the needle 121 may be bent around a smooth, rounded surface. The illustrated configuration may be achieved by replacing the cap 141 after bending the needle 121, as shown in FIG. 8, for example. This may be beneficial to a user because, unlike an injection device in a configuration in which a needle 121 is straight, the user may be able to replace the cap 141 without advancing the cap 141 toward the distal end 123 of the needle 121, thus decreasing the likelihood of the user being punctured by the needle 121. In some embodiments, the user may replace the cap 141 between a plurality of injections using the needle 121.

The illustrated assembly of FIG. 9 may also be configured prior to delivery of the injection device to the user. In some of these embodiments, the needle 121 may comprise a material that is shape set and configured to adjust to a desired bent angle when a compression pressure of the cap 141 is relieved by removing the cap 141. The desired angle may be any angle between 180 degrees and 0 degrees. In some embodiments, the desired angle is about 90 degrees. In other embodiments, the desired angle is about 45 degrees. In further embodiments, the desired angle is one of about 45 degrees and about 135 degrees.

FIG. 10 illustrates a needle guide 200 comprising a proximal end 201, a distal end 203, a protrusion having a top surface 204 and at least one side surface 206, an extension 208 extending from a surface of the distal end 203, a bending trough 209, an exterior surface 211 of a proximal segment of the body member 202 of the needle guide 200, an exterior surface 212 of a distal segment of the body member 202 of the needle guide 200, and a lumen 215. As further detailed below, the needle guide 200 may be utilized to facilitate bending of a medical device, such as a needle. The needle guide defines a longitudinal axis extending between the proximal end 201 and the distal end 203. As shown, the lumen 215 may be parallel to the longitudinal axis. Unless differences are specifically identified, elements of the needle guide 200 may have the same characteristics as similar elements described for needle guide 100. As shown in the illustration, the protrusion may be positioned opposite the bending trough 209 from the lumen 215. The top surface 204 may provide a surface upon which a user may push to insert the needle into a patient. The at least one side surface 206 may be used by a user to pull the needle guide 200 and retract the needle from the patient. The protrusion, when viewed from the top, may be rectangular as shown, or, in other embodiments, the protrusion may be any other shape including, but not limited to, circular, triangular, trapezoidal, star-shaped, or hourglass-shaped. As shown, a distal surface of the protrusion may be coplanar with the distal end 203. In other embodiments, the distal surface of the protrusion may be displaced proximally from the distal end 203. In still other embodiments, the protrusion may extend distal of the trough 209 along the longitudinal axis. In some embodiments, the needle guide 200 may have two or more protrusions.

FIG. 11 depicts the needle guide 200 of FIG. 10 from a perspective view of the proximal end 101 of the needle guide 200. In FIG. 11, the lumen 215 is shown extending into the body 202 of the needle guide 200 from the proximal end 101. An injection device interface 213 is also shown. The proximal end 201, the protrusion having the top surface 204 and the at least one side surface 206, the exterior surface 211 of the proximal segment of the body member 202 of the needle guide 200, the exterior surface 212 of the distal segment of the body member 202 of the needle guide 200, and the lumen 215 are also indicated.

The injection device interface 213 may be configured to couple the needle guide 200 to an injection device. In some embodiments, the injection device interface 213 may form a friction fit with a needle hub of the injection device. In other embodiments, the injection device interface 213 is configured to form a snap fit connection with a needle hub of the injection device. The injection device interface 213 may be configured in any shape to mate with an element of the injection device. In some embodiments, the injection device interface 213 restricts rotation of the needle guide 200 around the longitudinal axis (with respect to the injection device) when coupled to an injection device.

The lumen 215 may extend the length of the needle guide 200 and may be defined by an interior surface of the body member 202 of the needle guide 200. In some embodiments, a diameter of the lumen 215 may be slightly larger than a diameter of a needle to be bent, thus forming a loose fit around the needle. In the illustrated embodiment, the lumen 215 is in communication with the bending trough 209 as shown in FIG. 10.

FIG. 12 is a side view of the needle guide 200 of FIG. 10 illustrating the proximal end 201, the distal end 203, the protrusion comprising the top surface 204 and the at least one side surface 206, the extension 208 extending from the distal end 203, the exterior surface 211 of the proximal segment of the body member 202, and the exterior surface 212 of the distal segment of the body member 202. The length of the needle guide 200 may be any of the sizes or ranges of sizes disclosed for the length of the needle guide 100 above.

Figure 13:
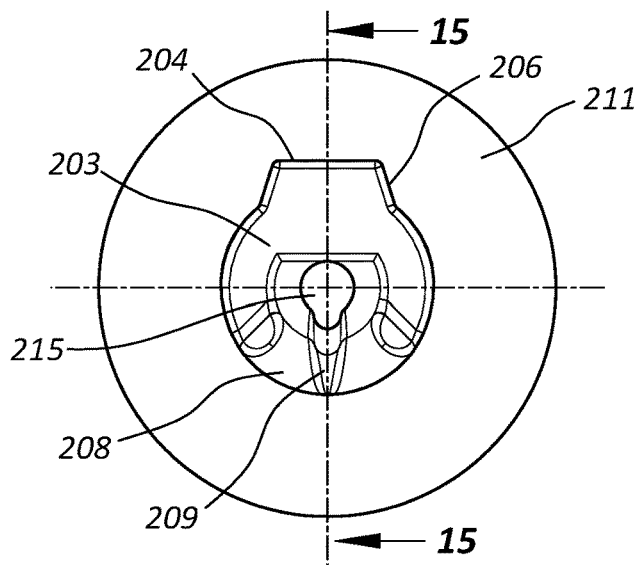
FIG. 13 is an end view of the needle guide of FIG. 10 from a distal end.

FIG. 13 is an end view of the distal end 203 of the needle guide 200 of FIG. 10 showing the protrusion comprising the top surface 204 and the at least one side surface 206, the extension 208, the bending trough 209, the exterior surface 211 of the proximal segment of the body of the needle guide 200, and the lumen 215. As shown, the exterior surface 211 of the proximal segment of the body of the needle guide 200 may be seen from the end view because, in the shown embodiment, the distal segment of the body member 202 of the needle guide 200 is narrower than the proximal segment of the body member 202 of the needle guide 200. Also shown is the bending trough 109 that may have a topography to direct the position of the needle to a proper bending location when bending a needle upon the bending trough 209.

Figure 14:
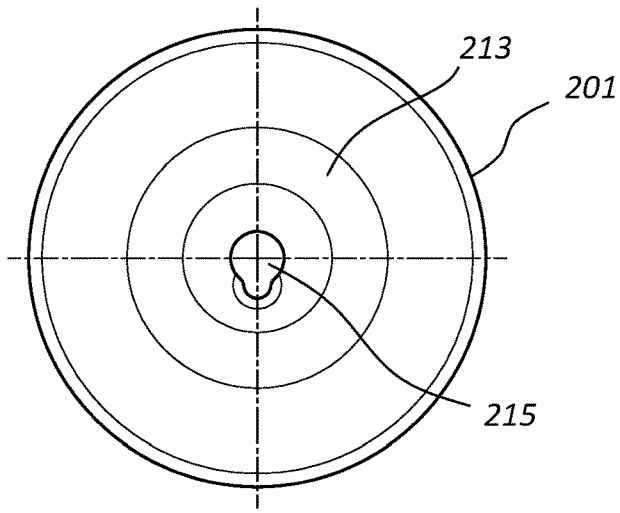
FIG. 14 is an end view of the needle guide of FIG. 10 from a proximal end.

FIG. 14 is an end view of the proximal end 201 of the needle guide 200 of FIG. 10 showing the injection device interface 213 and the lumen 215. As in the illustrated embodiment, the injection device interface 213 may extend a length distally from the proximal end 201 and terminate proximal of the distal end 203 of the needle guide 200. In the embodiment shown, the injection device interface 213 comprises a frusto-conical shape and a cylindrical shape. In other embodiments, the injection device interface 213 may comprise a combination of any shapes, including, but not limited to, any of the shapes described in this disclosure.

Figure 15:
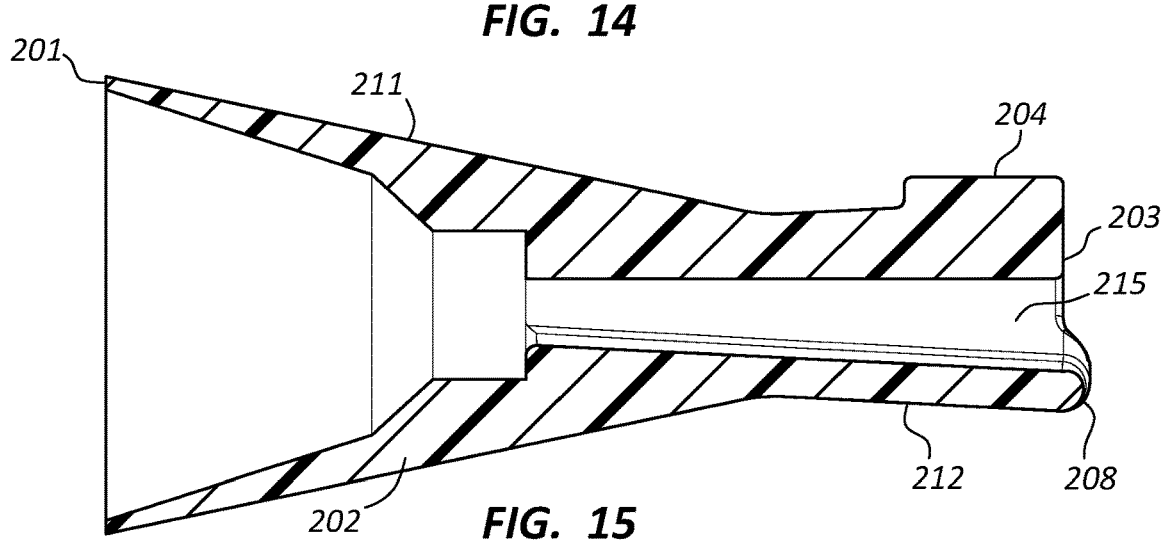
FIG. 15 is a cross-sectional view from the side of the needle guide of FIG. 10.

FIG. 15 is a cross-sectional view of the needle guide 200 along line 15 of FIG. 13 showing the proximal end 201, the distal end 203, the protrusion comprising the top surface 204 and the at least one side surface 206, the extension 208, the exterior surface 211 of the proximal segment of the body 202 of the needle guide 200, the exterior surface 212 of the distal segment of the body 202 of the needle guide 200, the injection device interface 213, and the lumen 215. As shown, a diameter of the lumen 215 may vary along the length of the needle guide 200. In some embodiments, the diameter of the lumen 215 is narrowest adjacent the bending trough 209.

Figure 16:
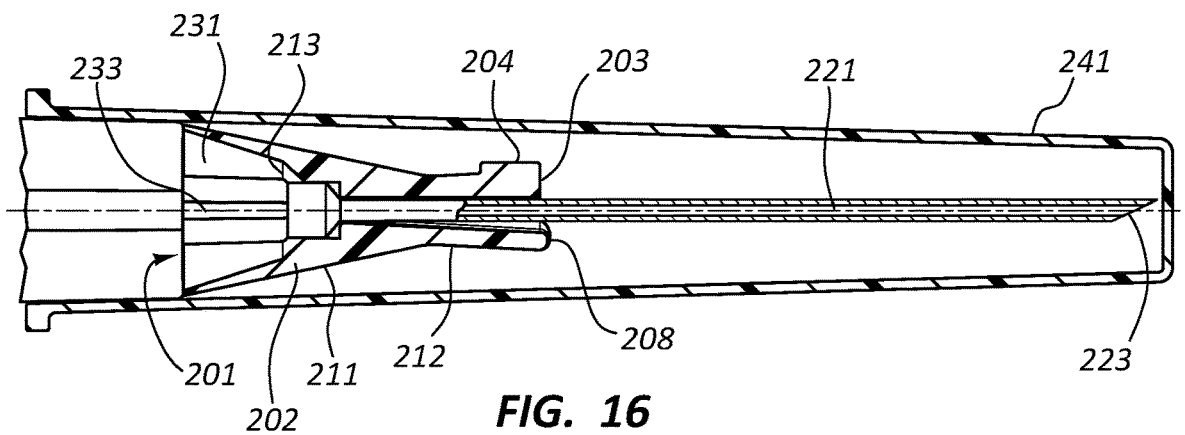
FIG. 16 is a cross-sectional view from the side of the needle guide of FIG. 10 assembled with a medical device.

FIG. 16 is a cross-sectional view of the needle guide 200 of FIG. 10 assembled with an injection device comprising a needle hub 231, a needle coupling region 233 wherein a needle 221 may be coupled to the needle hub 231, a distal end 223 of the needle 221, and a cap 241. As shown, the injection device interface 213 may interact to couple the needle guide 200 to the injection device. As in the description above relating to the assembly of FIG. 7, in some embodiments, the injection device interface 213 may loosely couple to the injection device. In other embodiments, the injection device interface 213 may couple to the injection device using one or more of a friction fit, a snap fit, a permanent weld, and an adhesive. In some embodiments, the needle guide 200 may encapsulate the needle hub 231 and the proximal end 201 may contact another element of the injection device. In other embodiments, a portion of the needle hub 231 may be visible proximal to the proximal end 201 of the needle guide 200. The needle 221 may be coupled to the coupling region 233 of the needle hub 231 using a rigid coupling system including, but not limited to, adhesive, melting, and/or welding.

Similar to embodiments of needle guide 100 described above, in some embodiments of needle hub 200, the needle guide 200 of may be integrally formed with the needle hub 231. For example, the needle guide 200 and the needle hub 231 may be formed of a single piece of material such as plastic or metal. In some of these embodiments, the needle 221 may be rigidly coupled to a proximal segment of the single piece of material and a distal segment may comprise the features described herein for the bending device 200, wherein the distal segment provides a distance to offset the proximal segment from the bending trough 209.

Figure 17:
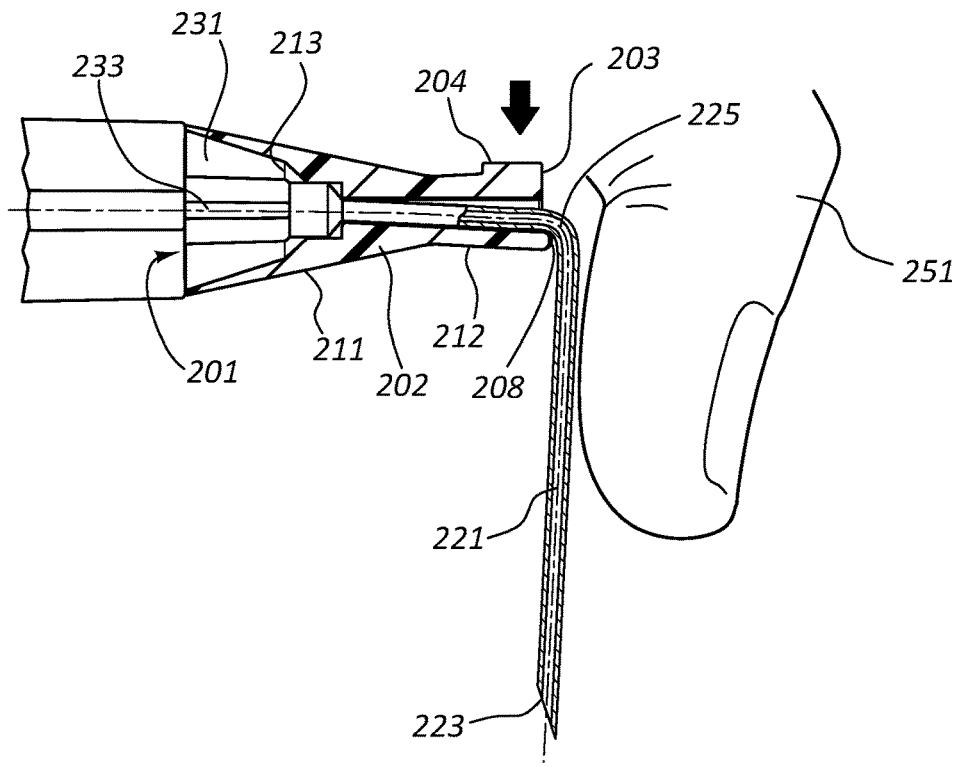
FIG. 17 is another cross-sectional view from the side of the needle guide and the medical device of FIG. 16.

FIG. 17 illustrates the assembly of FIG. 16 with the cap 241 removed and the needle 221 is bent by a user's finger 251. FIG. 17 further shows a bending region 225 bent upon the trough 209 of the needle guide 200. As in the illustrated embodiment, the trough 209 may cause the bending region 225 to follow the curve of the trough 209 to an angle approximately normal to the longitudinal axis of the needle guide 200. In other embodiments, a user may bend the needle 221 to any desired angle including about 30 degrees, about 45 degrees, about 60 degrees, about 120 degrees, about 135 degrees, and about 150 degrees. As shown in the illustration, a user's finger 251 may be used to apply a force on the needle 221 from a direction opposite the trough 209 to cause the needle 221 to bend upon the trough 209. The illustration also shows that the user's finger 251 may bend the needle 221 without being placed in proximity to the distal end 223 of the needle 221. In other embodiments, a user may bend the needle 221 by advancing the cap 241 distally and exerting a downward force on the cap 241 such that an interior surface of the cap 141 transfers the downward force onto the needle 221, thus bending the needle 221 without direct contact between the user and the needle 221. In other embodiments, a user may press the needle 221 against another surface to provide a normal force to bend the needle 221 upon the bending trough 209.

Figure 18:
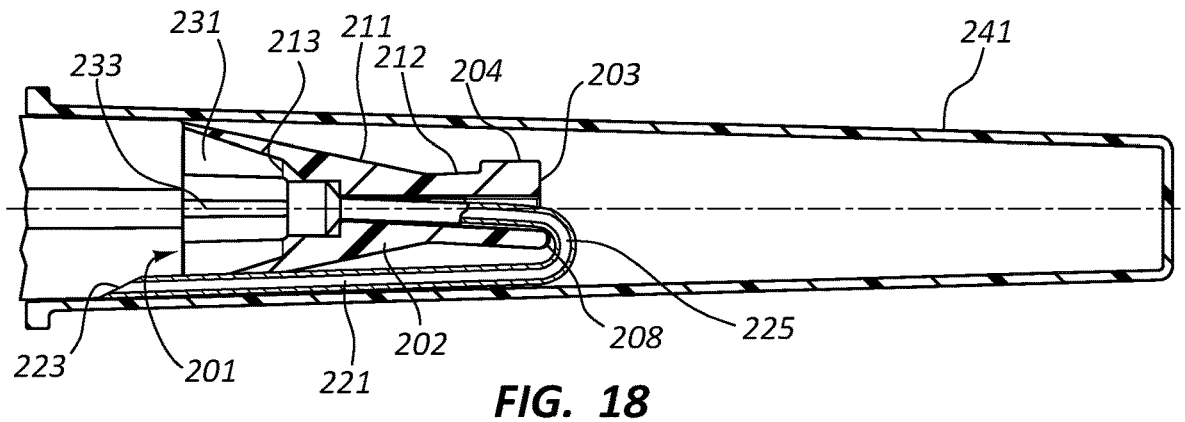
FIG. 18 is another cross-sectional view from the side of the needle guide and the bent medical device of FIG. 16.

FIG. 18 illustrates the assembly of FIG. 16 wherein the needle 221 is bent more than 90 degrees. In some embodiments, the needle guide 200 comprises a rounded surface connecting the bending trough 209 to the exterior surface 212 of the distal segment of the body of the needle guide 200 such that the needle 221 is bent around a smooth, rounded surface. In some embodiments, the extension 208 and the rounded surface together form a parabolic curve. In other embodiments, the extension 208 and the rounded surface form one of a semi-circle or an arc of an ellipse. The illustrated configuration may be achieved by replacing the cap 241 after bending the needle 221 as shown in FIG. 17. Some potential benefits of this configuration are described above.

The illustrated assembly of FIG. 18 may also be configured prior to delivery of the injection device to the user. In some of these embodiments, the needle 221 may comprise a material that is shape set and configured to adjust to a desired bent angle when a compression pressure of the cap 141 is relieved by removing the cap 241. The desired angle may be any angle between 180 degrees and 0 degrees. In some embodiments, the desired angle is about 30 degrees, about 60 degrees, about 90 degrees, about 120 degrees, about 150 degrees, about 45 degrees, or about 135 degrees.

Figure 19:
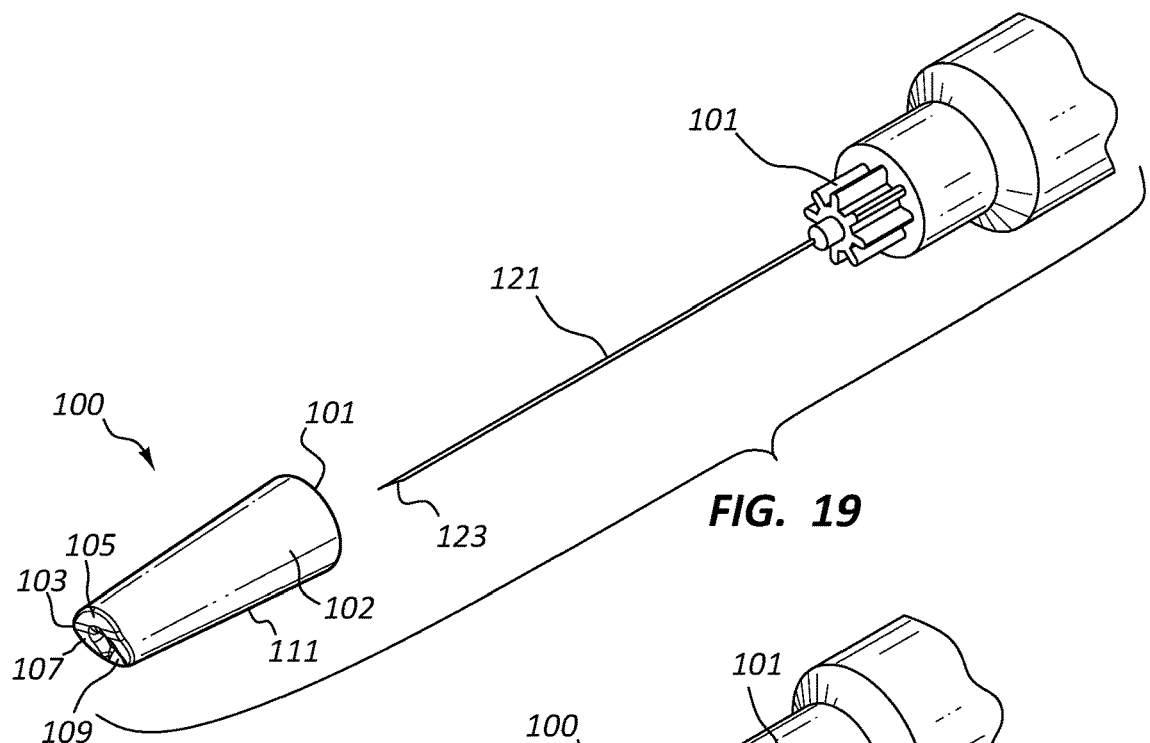
FIG. 19 is a perspective view of the needle guide of FIG. 1 with a syringe.

FIG. 19 illustrates the needle guide 100 of FIG. 1 distal of the distal end 123 of a needle 121 comprised in an injection device. As illustrated, the injection device may comprise a needle hub 131. In other embodiments, the needle hub 131 may be integrally formed with the needle guide 100. As shown, the needle guide 100 may be oriented such that the proximal end 101 of the needle guide 100 is adjacent the distal end 123 of the needle 121.

Figure 20:
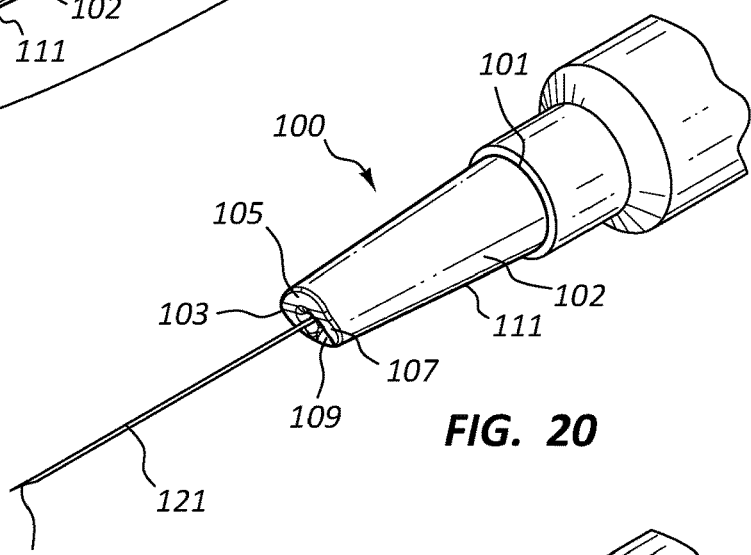
FIG. 20 is a perspective view of the needle guide and syringe of FIG. 19 assembled together.

FIG. 20 illustrates the needle guide 100 and the injection device of FIG. 19 in an assembled configuration. In the assembled configuration, the needle guide 100 is advanced along the needle 121 proximally until the proximal end 101 is adjacent the needle hub 131 of the injection device, and the distal end 123 of the needle 121 extends through the lumen (not shown) and the distal end 123 of the needle 121 extends distally from the distal-most surface 105 of the distal end 103 of the needle guide 100. In some embodiments, the needle guide 100 is coupled to the needle hub 131 using any of the methods described herein.

Figure 21:
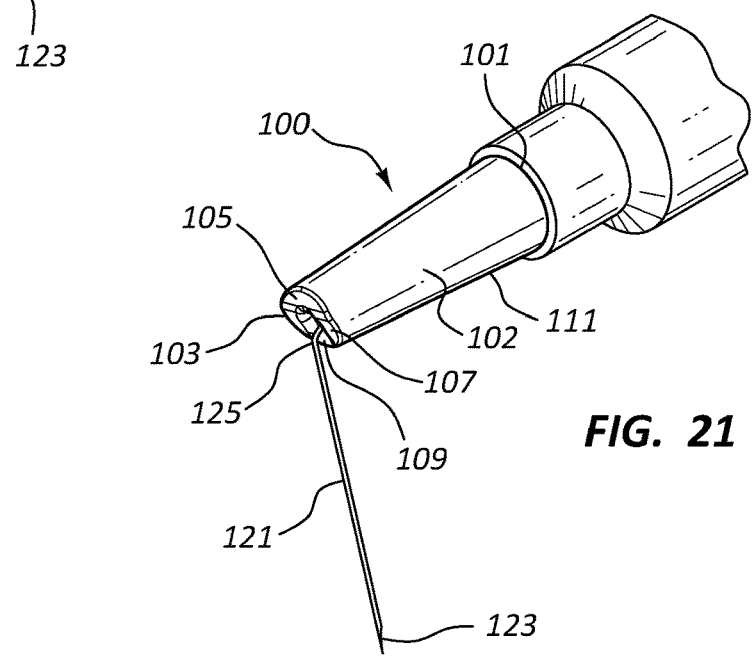
FIG. 21 is a perspective view of the assembled needle guide and syringe of FIG. 20 after a needle of the syringe has been bent.

FIG. 21 illustrates the assembly of FIG. 20 with the needle 121 bent upon the bending trough 109 of the needle guide 100. In the illustrated configuration, the needle 121 may be ready for insertion into a patient. As described herein, the needle 121 may be bent to any desired angle between 0 and 180 degrees.

Figure 22:
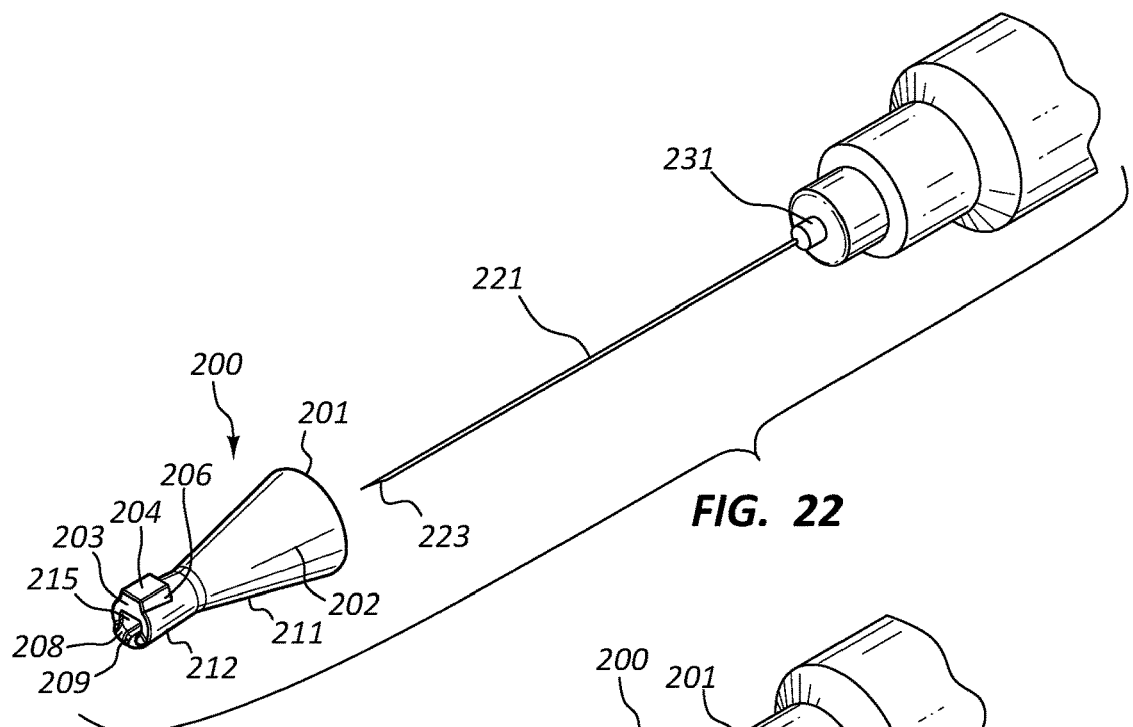
FIG. 22 is a perspective view of the needle guide of FIG. 10 with a syringe.

FIG. 22 illustrates the needle guide 200 of FIG. 10 distal of the distal end 223 of a needle 221 comprised in an injection device. The injection device may also comprise a needle hub 231. In other embodiments, the needle hub 131 may be integrally formed with the needle guide 200. As illustrated, the needle guide 200 may be oriented such that the proximal end of 201 of the needle guide 200 is adjacent the distal end 223 of the needle 221.

Figure 23:
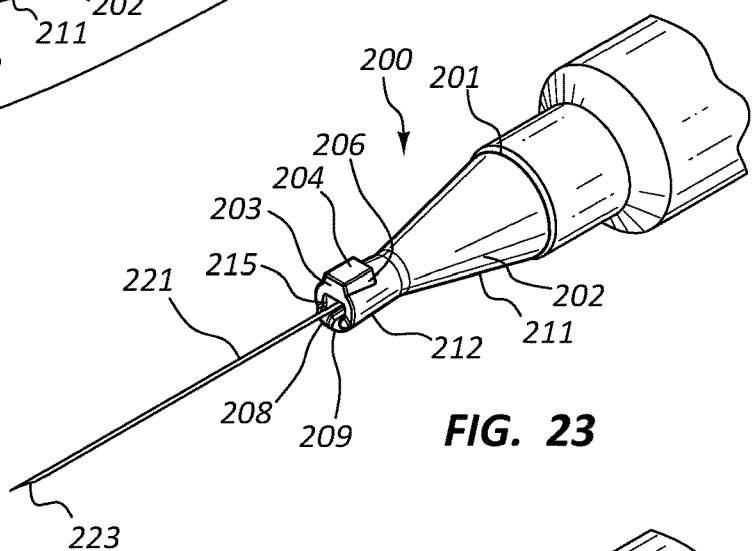
FIG. 23 is a perspective view of the needle guide and syringe of FIG. 22 assembled together.

FIG. 23 illustrates the needle guide 200 and the injection device of FIG. 22 in an assembled configuration. In the assembled configuration, the needle guide 200 is advanced along the needle 221 proximally until the proximal end 201 is adjacent the needle hub 231 of the injection device, and the distal end 223 of the needle 221 extends through the lumen (not shown) and the distal end 223 of the needle 221 extends distally from the extension 208. In some embodiments, the needle guide 200 is coupled to the needle hub 231 using any of the methods described herein.

Figure 24:
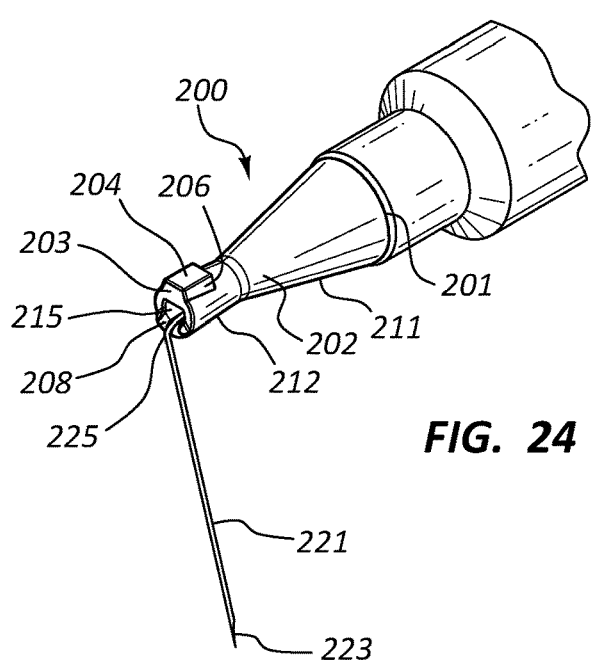
FIG. 24 is a perspective view of the assembled needle guide and syringe of FIG. 23 after a needle of the syringe has been bent.

FIG. 24 illustrates the needle guide 200 and the injection device of FIG. 23 the needle 221 bent upon the bending trough 209 of the needle guide 200. In the illustrated configuration, the needle 221 may be ready for insertion into a patient. As described herein, the needle 221 may be bent to any desired angle between 0 and 180 degrees.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings, and the appended claims. In addition to variations and modifications in the component parts and/or arrangements, alternative uses will also be apparent to those skilled in the art. The scope of the present invention should, therefore, be determined only by the following claims.

The invention claimed is:

1. A device for bending a needle fixed to a needle hub of an injection device for use thereof, the device comprising:
a body member extending between a proximal end of the device and a distal end of the device, the device having a first opening at the proximal end of the device and a second opening at the distal end of the device, the body member defining a lumen with a lumen diameter disposed within the body member, the distal end of the device being located a distance from the proximal end of the device along a longitudinal axis, wherein the lumen extends between the first opening and the second opening, and an interior surface of the first opening at the proximal end of the device comprises an injection device interface having an inner dimension that is larger than the lumen diameter, the injection device interface configured to receive the needle hub of the injection device, wherein the needle hub has an outer diameter that is larger than the lumen diameter; and
a bending trough extending adjacent the distal end of the device, the bending trough defining at least a portion of the second opening of the device, the bending trough being in communication with the lumen and having a trough width that widens adjacent the distal end, wherein the bending trough is configured to provide a guide for bending the needle.

2. The device of claim 1, wherein the bending trough defines a convexly curved surface configured for supporting a bend in the needle.

3. The device of claim 1, wherein the bending trough is positioned proximal of a distal-most surface of the body member.

4. The device of claim 1, wherein the body member comprises a frusto-conical shape.

5. The device of claim 1, wherein the body member comprises a plurality of cross-sectionally bulbous segments and at least one narrow segment connecting the plurality of bulbous segments.

6. The device of claim 1, wherein the distal end of the device comprises a truncated surface, wherein a distal end of the bending trough comprises a concave portion surrounded by the truncated surface.

7. The device of claim 1, wherein the bending trough comprises a concave surface, wherein a distal end of the concave surface of the bending trough is angled substantially perpendicular to a proximal portion of the concave surface of the bending trough.

8. The device of claim 1, wherein the lumen is a cavity.

9. The device of claim 1, wherein the lumen is a tubular channel.

10. The device of claim 1, wherein said proximal end of the device further comprises:
said first opening in communication with the lumen, wherein the first opening is configured to receive said needle; and
wherein the injection device interface further comprises a plurality of engagement grooves spanning from the first opening and configured to receive a corresponding engagement protrusion of the needle hub.

11. The device of claim 1, wherein the injection device interface is configured to couple with the needle hub while at least a portion of the needle of the injection device protrudes through the second opening so that a user may bend at least a portion of the needle by pressing on a portion of the needle that protrudes through the second opening.

12. A device for bending a needle fixed to a needle hub of an injection device, the device comprising:

a body member extending between a first end of the device and a second end of the device, the body member having a passage extending in a first axial direction, the passage having a first opening at the first end of the device and a second opening at the second end of the device; and a bending trough forming a portion of the second opening of the passage, the bending trough having a widened portion that widens adjacent the second end of the device, wherein the first opening at the first end of the device comprises an injection device interface with a larger diameter than a bending trough diameter and that is configured to interface with a portion of the needle hub that has an outer diameter that is larger than the bending trough diameter while the needle of the injection device protrudes through the second opening, the bending trough being configured for a non-destructive bending of at least a portion of the needle.

13. The device of claim 12, wherein the injection device interface is configured to couple with the needle hub while at least a portion of the needle of the injection device protrudes through the second opening so that a user may bend at least a portion of the needle by pressing on a portion of the needle that protrudes through the second opening.

* * * * *